US011014919B2

(12) United States Patent
Cabri et al.

(10) Patent No.: US 11,014,919 B2
(45) Date of Patent: May 25, 2021

(54) PROCESS FOR THE PREPARATION OF ALECTINIB

(71) Applicants: FRESENIUS KABI IPSUM S.R.L., Cassina de' Pecchi-Milan (IT); Alma Mater Studiorum - Università di Bologna, Bologna (IT)

(72) Inventors: Walter Cabri, Cassina de' Pecchi - Milan (IT); Alessandra Tolomelli, Bologna (IT); Assunta De Nisi, Bologna (IT); Lucia Ferrazzano, Bologna (IT)

(73) Assignees: Fresenius Kabi IPSUM S.r.l., Milan (IT); Alma Mater Studiorum—Università di Bologna, Bologna (IT)

( * ) Notice: Subject to any disclaimer, the term of this patent is extended or adjusted under 35 U.S.C. 154(b) by 0 days.

(21) Appl. No.: 16/705,275

(22) Filed: Dec. 6, 2019

(65) Prior Publication Data

US 2020/0181133 A1    Jun. 11, 2020

(30) Foreign Application Priority Data

Dec. 7, 2018  (EP) ..................................... 18211036
Jul. 4, 2019  (EP) ..................................... 19184409

(51) Int. Cl.
*C07D 413/14*    (2006.01)

(52) U.S. Cl.
CPC .................................. *C07D 413/14* (2013.01)

(58) Field of Classification Search
CPC .................................................. C07D 413/14
See application file for complete search history.

(56) References Cited

U.S. PATENT DOCUMENTS

| | | | |
|---|---|---|---|
| 9,126,931 B2 | 9/2015 | Kinoshita et al. | |
| 9,365,514 B2 | 6/2016 | Furumoto et al. | |
| 9,440,922 B2 | 9/2016 | Kinoshita et al. | |
| 9,573,932 B2 | 2/2017 | Xu | |
| 10,221,155 B2 | 5/2019 | Xu | |
| 10,344,014 B2 | 7/2019 | Shiraki et al. | |
| 10,646,468 B2 | 5/2020 | Furumoto et al. | |
| 2012/0083488 A1 | 4/2012 | Kinoshita et al. | |
| 2013/0143877 A1 | 6/2013 | Furumoto et al. | |
| 2015/0150845 A1 | 6/2015 | Kinoshita et al. | |
| 2016/0257667 A1 | 9/2016 | Xu | |
| 2016/0317494 A1 | 11/2016 | Furumoto et al. | |
| 2016/0340308 A1 | 11/2016 | Kinoshita et al. | |
| 2017/0217927 A1 | 8/2017 | Shiraki et al. | |
| 2019/0284163 A1 | 9/2019 | Shiraki et al. | |
| 2020/0017442 A1 | 1/2020 | Kinoshita et al. | |

FOREIGN PATENT DOCUMENTS

| | | |
|---|---|---|
| CN | 105777710 A | 7/2016 |
| CN | 106518842 A | 3/2017 |
| CN | 106892861 A | 6/2017 |
| CN | 106905226 A | 6/2017 |
| CN | 106928125 A | 7/2017 |
| CN | 106928185 A | 7/2017 |
| CN | 106995433 A | 8/2017 |
| CN | 107011245 A | 8/2017 |
| CN | 107129488 A | 9/2017 |
| CN | 107987056 A | 5/2018 |
| CN | 108033947 A | 5/2018 |
| CN | 108178743 A | 6/2018 |
| CN | 108314674 A | 7/2018 |
| CN | 108264476 A | 10/2018 |
| CN | 109293629 A | 2/2019 |
| CN | 109384664 A | 2/2019 |
| CN | 109438218 A | 3/2019 |
| CN | 106892860 B | 8/2019 |
| CN | 106928184 B | 9/2019 |
| CN | 107033124 B | 9/2019 |
| CN | 107033125 B | 9/2019 |
| EP | 2 441 753 A1 | 4/2012 |
| EP | 3 135 671 A1 | 3/2017 |
| EP | 3 556 754 1 | 10/2019 |
| IN | 201741044856 A | 6/2019 |
| WO | WO 2010/143664 A1 | 12/2010 |
| WO | WO 2012/023597 A1 | 2/2012 |
| WO | WO 2015/163447 A1 | 10/2015 |
| WO | WO 2016/021707 A1 | 2/2016 |
| WO | WO 2019/008520 A1 | 1/2019 |
| WO | WO 2019/038779 A1 | 2/2019 |
| WO | WO 2019/211868 A1 | 11/2019 |

OTHER PUBLICATIONS

Anonymous, "Preparation of 9-ethyl-6,6-dimethyl-8-(4-morpholinopiperidin-1-yl)-11-oxo-6,11-dihydro-5H-benzo[b]carbazole-3-carbonitrile", Ip.coM Journal 17(7A): 1-2 (2017).
Austin et al., "Facile synthesis of ethynylated benzoic acid derivatives and aromatic compounds via ethynyltrimethylsilane," *J. Org. Chem.*, 46(11): 2280-2286 (1981).
Flick et al., "Synthetic approaches to the 2014 new drugs," *Bioorg. Med. Chem.*, 24(9): 1937-1980 (2016).
Herbert, "Negishi-type coupling of bromoarenes with dimethylzinc," *Tet. Let.*, 45: 817-819 (2004).
Hughes, "Patent Review of Manufacturing Routes to Recently Approved Oncology Drugs: Ibrutinib, Cobimetinib, and Alectinib," *Org. Process Res. Dev.*, 20(11): 1855-1869 (2016).
Kinoshita et al., "Design and synthesis of a highly selective, orally active and potent anaplastic lymphoma kinase inhibitor (CH5424802)," *Bioorg. Med. Chem.*, 20(3): 1271-1280 (2012).
Kinoshita et al., "9-Substituted 6,6-Dimethyl-11-oxo-6,11-dihydro-5H-benzo[b]carbazoles as Highly Selective and Potent Anaplastic Lymphoma Kinase Inhibitors," *J. Med. Chem.*, 54(18): 6286-6294 (2011).
Leadbeater et al., "Rapid, easy copper-free Sonogashira couplings using aryl iodides and activated aryl bromides," *Tetrahedron Letters* 44: 8653-8656 (2003).
*Reaxys Database*, Elsevier Lif Sci IP Ltd, XP002784398, Accession No. 46135094. (Aug 1, 2017)—1 pg.
European Patent Office, International Search Report in International Application No. PCT/IB2018/054932 (dated Jan. 2, 2019).

(Continued)

*Primary Examiner* — Rebecca L Anderson
(74) *Attorney, Agent, or Firm* — Leydig, Voit & Mayer, Ltd.

(57) ABSTRACT

The present invention relates to a process for preparing alectinib, or a pharmaceutically acceptable salt thereof, and to related intermediates.

16 Claims, No Drawings

(56) References Cited

OTHER PUBLICATIONS

European Patent Office, Written Opinion in International Application No. PCT/IB2018/054932 (dated Jan. 2, 2019).
International Bureau of WIPO, International Preliminary Report on Patentability —Chapter I—in International Application No. PCT/IB2018/054932 (dated Jan. 7, 2020).
European Patent Office, Extended European Search Report in European Patent Application No. 19 18 4409.1 (dated Sep. 12, 2019).
U.S. Appl. No. 16/627,160, filed Dec. 27, 2019.

PROCESS FOR THE PREPARATION OF ALECTINIB

CROSS-REFERENCE TO RELATED APPLICATIONS

This application claims the benefit of European Patent Application No. 19184409.1, filed Jul. 4, 2019, and European Patent Application No. 18211036, filed on Dec. 7, 2018, the disclosures of which are incorporated herein by reference in their entireties for all purposes.

FIELD OF THE INVENTION

The present invention relates to a process for preparing alectinib or a pharmaceutically acceptable salt thereof. The present invention also relates to intermediate compounds which are useful in such process and to the preparation of such intermediate compounds.

BACKGROUND OF THE INVENTION

Alectinib, chemically known as 9-ethyl-6,6-dimethyl-8-(4-morpholin-4-yl-piperidin-1-yl)-11-oxo-6,11-dihydro-5H-benzo[b]carbazole-3-carbonitrile, is represented by formula I.

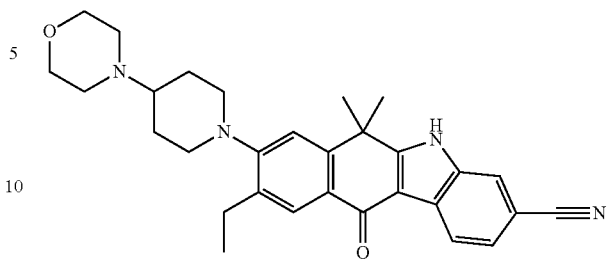

I

Alectinib is approved as the hydrochloride salt, which is the active ingredient of drug Alecensa® and is intended for oral administration in the form of capsule. It is an anaplastic lymphoma kinase (ALK) inhibitor indicated for the treatment of patients with non-small-cell lung cancer (NSCLC).

Alectinib, as represented by formula I, and its hydrochloride salt were described in WO2010/143664. Example 366 of this PCT application describes the preparation of alectinib and its hydrochloride salt as depicted in scheme 1:

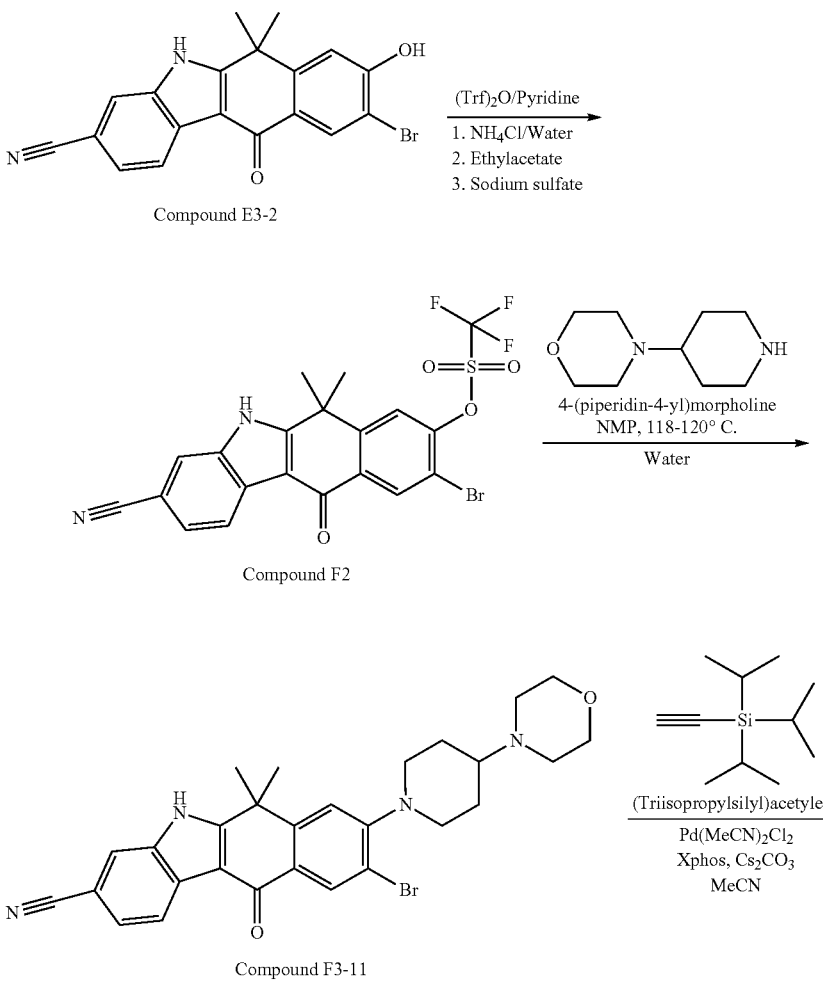

Scheme 1

-continued

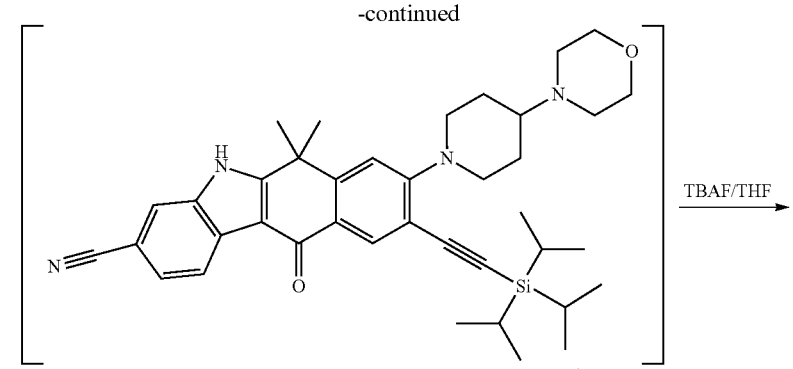

TBAF/THF

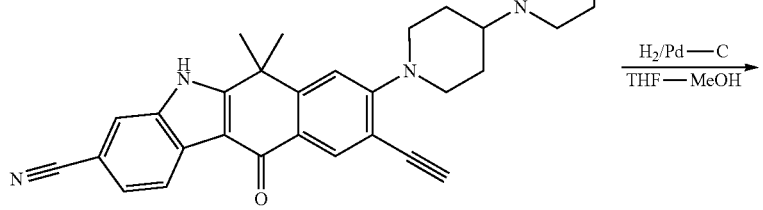

Compound F5-49

H₂/Pd—C
─────────
THF—MeOH

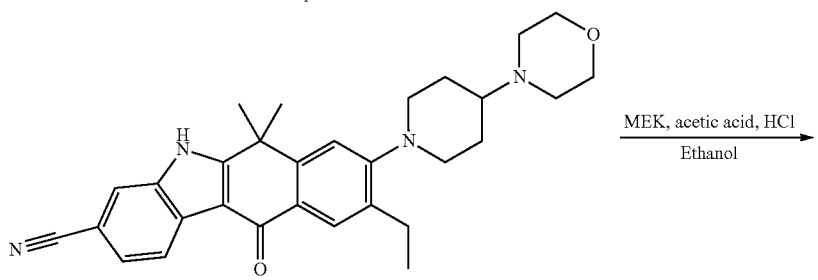

Alectinib
Formula (I)

MEK, acetic acid, HCl
────────────────────
Ethanol

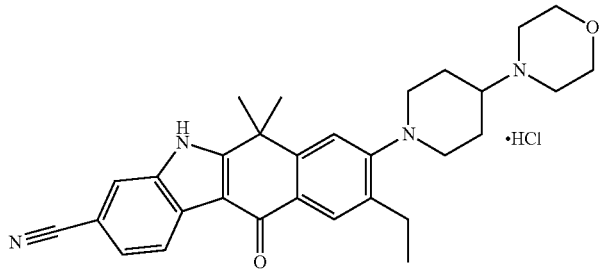

Alectinib Hydrochloride

Kinoshita et al., *Bioorg. Med. Chem.*, 2012, 20, 1271-1280 also reports the preparation of alectinib using the above process and provides the reaction yields.

In the above process, alectinib hydrochloride was prepared starting from compound E3-2 using a six-step process, which has a total pretty low yield (approx. 8.8%).

Specifically, introduction of ethyl group in the compound F3-11 involves a three step process: first, the conversion of bromine into ethynyl group, through the triisopropylsilyl-protected derivative, then cleavage of triisopropylsilyl group (TIPS), and, finally, reduction by catalytic hydrogenation of ethynyl to ethyl group.

The above mentioned three step process for the introduction of ethyl group has several disadvantages: it employs some expensive and toxic reagents and has a low total yield (approx. 14%).

In particular, the conversion of the bromine into triisopropylsilyl-protected ethynyl is carried out through coupling with expensive triisopropylsilylacetylene and involves the use of toxic tetra-n-butylammonium fluoride (TBAF) as reagent for TIPS protection cleavage.

Therefore, there still remains a need to improve such process and develop an efficient, simple and industrially viable synthetic route, which can overcome the drawbacks of the prior art. It is of particular importance to develop a method that would allow for an increase in yield for particular steps, which in turn would lead to an increase in the yield of the whole technology.

In order to overcome the problems associated with the prior art, it is herein described a new and improved process which provides alectinib, or a pharmaceutically acceptable salt thereof, in higher yield using cheaper and less toxic reagents.

SUMMARY OF THE INVENTION

It has been developed a process for the preparation of alectinib of formula I,

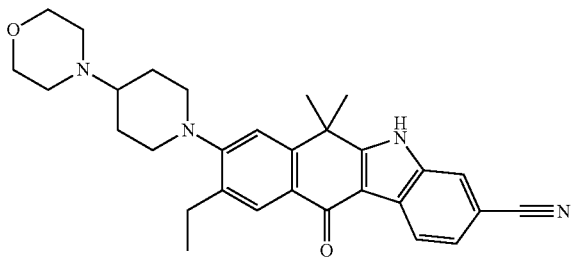

I or a pharmaceutically acceptable salt thereof, which comprises the steps of:
a) reacting a compound of formula IV

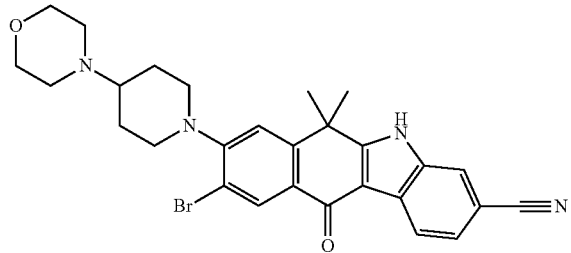

IV with trimethylsilylacetylene (TMS-acetylene) in the presence of a base, a palladium catalyst and a ligand;
b) treating the resulting intermediate compound of formula III

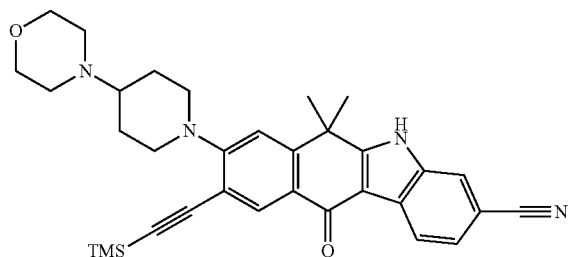

III with a base, such as $K_2CO_3$, in the presence of a solvent, for instance an alcohol solvent, such as methanol, and c) converting the resulting intermediate compound of formula II

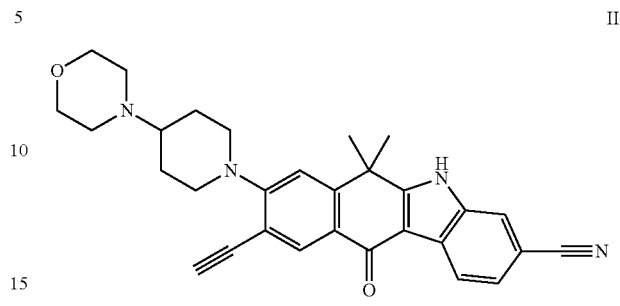

II sinto alectinib, or a pharmaceutically acceptable salt thereof, preferably the hydrochloride salt, by reduction of the ethynyl group.

The above process is preferably carried out by isolating all intermediate compounds, namely intermediate compounds of formula III and II. Also preferably, the process is carried out without isolating intermediate compound of formula III. Even more preferably, the above process is carried out as a one-pot reaction, that is, without the need to isolate any of the intermediate compounds of formula III and II, but completing the whole conversion directly to alectinib, or a pharmaceutically acceptable salt thereof, preferably the hydrochloride salt.

Definitions

The following definitions are used in connection with the present application, unless it is indicated otherwise.

The term "room temperature" refers to a temperature ranging from about 15° C. to 35° C., preferably to a temperature ranging from about 20° C. to 30° C., more preferably to a temperature of 25° C.

The terms "comprising" and "comprises" mean the elements recited, or their equivalents in structure or function, plus any other element or elements which are not recited.

The terms "having" and "including" are also to be construed as open ended. All ranges recited herein include the endpoints, including those that recite a range between two values. Whether so indicated or not, all values recited herein are approximate as defined by the circumstances, including the degree of expected experimental error, technique error, and instrument error for a given technique used to measure a value.

The term "optional" or "optionally" is taken to mean that the event or circumstance described in the specification may or may not occur, and that the description includes instances where the event occurs and instances where it does not.

As used herein, the term "contacting" includes mixing, adding, slurring, stirring or a combination thereof.

As used herein, the term "about" is to be construed as modifying a term or value such that it is not an absolute. Such term will be defined by the circumstances. This includes, at the very least, the degree of expected experimental error, technique error and instrument error for a given technique used to measure a value.

The term "pharmaceutically acceptable salts", includes, for example salts with an inorganic acid, e.g. hydrochloric acid, hydroiodic acid, phosphoric acid, phosphonic acid, sulfuric acid, hydrobromic acid or an organic acid, e.g. a carboxylic acid such as formic acid, acetic acid, citric acid, malic acid, maleic acid, tartaric acid, succinic acid, salicylic acid, trifluoroacetic acid, trichloroacetic acid, oxalic acid, benzoic acid or a sulfonic acid such as p-toluene sulfonic acid or methanesulfonic acid.

Abbreviations

DMF N,N-dimethylformamide dppb 1,4-bis(diphenylphosphino)butane dppf 1,1'-bis(diphenylphosphino)ferrocene dppe 1,2-bis(diphenylphosphino)ethane dppp 1,3-bis(diphenylphosphino)propane eq. equivalents HPLC High Performance Liquid Chromatography MeOH methanol $PdCl_2$ palladium(II) dichloride or dichloropalladium(II)

TBAF tetra-butylammonium fluoride

TEA triethylamine

TIPS triisopropylsilyl

TMS trimethylsilyl

XPhos 2-Dicyclohexylphosphino-2',4',6'-triisopropylbiphenyl

DETAILED DESCRIPTION OF THE INVENTION

The introduction of ethyl group in the compound of formula IV (F3-11 in the cited prior art) has been found to conveniently proceed by using trimethylsilyl-acetylene, as a replacement of triisopropylsilylacetylene. The trimethylsilyl group protection of intermediate compound of formula III is then cleaved in mild conditions by using a base in a solvent, for instance an alcohol solvent. Finally, the ethynyl group of intermediate compound of formula II is converted into ethyl group by reduction, for instance by catalytic hydrogenation, thus leading to the final compound, i.e. alectinib.

This process has several advantages. Trimethylsilylacetylene is much cheaper than triisopropylsilylacetylene. In addition, intermediate compound of formula III can be cleaved by using milder and cheaper reaction conditions: the use of toxic TBAF is avoided, as it is replaced by a base, such as an inorganic base. Furthermore, a cheap solvent, such as an alcohol solvent, is typically used instead of expensive THF. As a consequence, the new process is safer, cheaper and greener than the prior art. Such new process is therefore more cost-effective; furthermore, it is simple and efficient, and thus suitable for plant scale production. In addition, the present process for the preparation of alectinib through the introduction of the ethyl group in the intermediate compound of formula IV provides an improved process also in terms of chemical yield with respect to the prior art.

In a first aspect, the present invention provides a process for preparing alectinib, which comprises the following steps, a), b) and c).

Step a): Reacting a Compound of Formula IV

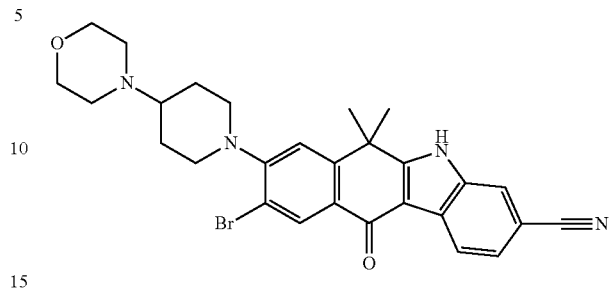

IV with trimethylsilylacetylene in the presence of a base, a palladium catalyst and a ligand, preferably in a suitable solvent, to obtain the intermediate compound of formula III, as defined above.

Preferably, the base is an organic base, which can be selected from the group consisting of triethylamine (TEA), diisopropylethylamine (DIEA), pyrrolidine, piperidine, N-methylmorpholine, tetramethylguanidine (TMG), 1,8-diazabicyclo-[5.4.0]undec-7-ene (DBU), 1,4-diazabicyclo[2.2.2]octane (DABCO), and N,N,N',N'-tetramethylethylenediamine. More preferably the base is TEA.

Step a) is carried out in the presence of a catalyst. The catalyst is preferably a palladium(II) or a palladium(0) catalyst, and it is typically used in association with a ligand, which can be a separate reagent or can be comprised in the palladium catalyst reagent. The ligand is preferably selected from the group consisting of triphenylphosphine ($PPh_3$), 1,1'-bis(diphenylphosphino)ferrocene (dppf), 1,2-bis(diphenylphosphino)ethane (dppe), 1,3-bis(diphenylphosphino)propane (dppp), 1,4-bis(diphenylphosphino)butane (dppb), tricyclohexylphosphine ($PCy_3$), 2-(dicyclohexylphosphino)biphenyl, tri-tert-butylphosphine ($tBu_3P$), $tBu_3PH \cdot BF_4$, 4,5-Bis(diphenylphosphino)-9,9-dimethylxanthene and 2-dicyclohexylphosphino-2',4',6'-triisopropylbiphenyl (XPhos). Preferably, the palladium catalyst is selected from the group consisting of $Pd(OAc)_2$, $PdCl_2$, $PdCl(PhCN)_2$, $PdCl_2(MeCN)_2$, $PdCl_2(PCy_3)_2$, $Pd(tBu_3P)_2$, $Pd(PPh_3)_4$, $PdCl_2(PPh_3)_2$, $PdCl_2(dppf)$, $PdCl_2(dppe)$, $PdCl_2(dppp)$ and $PdCl_2$/XPhos.

Particularly preferably, the catalyst in combination with the ligand is selected from the group consisting of $PdCl_2(PPh_3)_2$, $PdCl_2(dppf)$ and $PdCl_2$/XPhos.

Even more preferably, step a) is carried out in the presence of $PdCl_2(PPh_3)_2$.

The palladium catalyst is preferably used in an amount in the range of from 1 to 30 mol %, more preferably 1 to 20 mol %, even more preferably 1 to 10 mol %, particularly preferably 2 to 5 mol %, with respect to the compound of formula IV.

The ligand is preferably used in an amount in the range of from 1 to 30 mol %, more preferably 1 to 20 mol %, even more preferably 2 to 10 mol %, with respect to the compound of formula IV.

Step a) is typically carried out in the presence of a solvent. The solvent is preferably an organic solvent, which is more preferably selected from the group consisting of N-alkylpyrrolidones, like 1-octyl-2-pyrrolidone, 1-cyclohexyl-2-pyrrolidone, 1-(2-hydroxyethyl)-2-pyrrolidone, 1-benzyl-2-pyrrolidinone and N-methylpyrrolidone, N,N-dimethylacetamide, N,N-diethylacetamide, N,N-dimethylformamide (DMF), dimethylsulfoxide (DMSO), dioxane, acetonitrile, tetrahydrofuran or mixtures thereof. More preferably step a) is carried out in DMF or in an N-alkylpyrrolidone, selected from 1-octyl-2-pyrrolidone, 1-cyclohexyl-2-pyrrolidone, 1-(2-hydroxyethyl)-2-pyrrolidone, 1-benzyl-2-pyrrolidinone and N-methylpyrrolidone, or mixtures thereof.

Step a) is preferably carried out at a temperature in the range 50-100° C., preferably in the range 70-90° C., more preferably in the range 75-85° C., for instance at about 80° C.

Step b): Treating the Resulting Intermediate Compound of Formula III

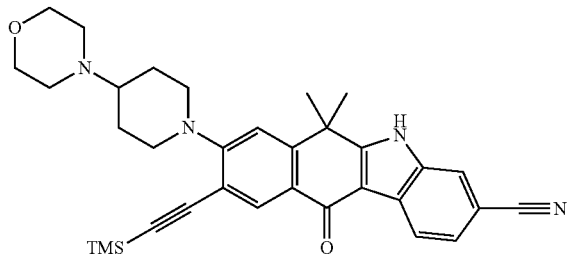

III with a base to cleave the trimethylsilyl group, to obtain the intermediate compound of formula II, as defined above.

Preferably, the base is an inorganic base, which can be selected from the group consisting of KOH, NaOH, $Na_2CO_3$, $Cs_2CO_3$ and $K_2CO_3$. More preferably, the inorganic base is $K_2CO_3$.

The inorganic base is preferably used in an excess amount, for instance in an amount in the range of from 1 to 4 eq., for instance 3 eq.

Step b) is typically carried out in a suitable solvent, preferably an alcohol solvent, like for instance methanol, ethanol, isopropanol or the like, at room temperature, as defined above. Preferably, step b is carried out in methanol.

A further aspect of the present invention is therefore a compound of formula III as defined above and its use in the preparation of alectinib (I).

Step c): Converting the Resulting Intermediate Compound of Formula II

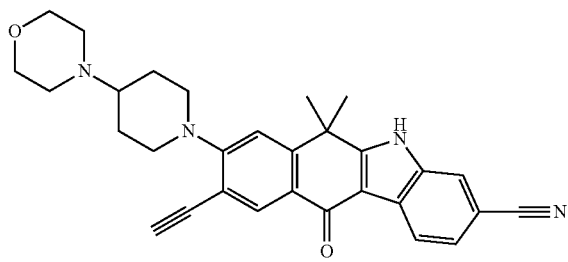

II into alectinib, or a pharmaceutically acceptable salt thereof, by reduction of the ethynyl group to ethyl group.

The reduction step c) is for instance carried out by catalytic hydrogenation, in an autoclave with hydrogen ($H_2$) under pressure, or by using a reducing reagent.

In a catalytic hydrogenation, the catalyst used is a suitable hydrogenation catalyst as, for instance, a palladium catalyst, like Pd/C 10%, tris-(dibenzylideneacetone) dipalladium(0), $Pd/Al_2O_3$ and $Pd/BaSO_4$, in a suitable amount, for instance in the range 5-30 mol %. Preferably, Pd/C 10% is used, for instance in an amount of about 10 mol %. The hydrogen pressure is typically in the range 1 to 5 bar pressure, preferably in the range 2 to 3 bar, for instance at about 2.5 bar pressure.

The catalytic hydrogenation is carried out in a suitable solvent, for instance in an organic solvent, such as THF, DMF, ethyl acetate, hexane, 1,4-dioxane, acetonitrile, water, toluene, methanol, ethanol, and the like, or mixtures thereof.

As a preferred aspect, the present invention provides a process wherein step a) is carried out at a temperature in the range 70-90° C. and the base is an organic base, such as triethylamine; step b) is carried out in an alcohol solvent, such as methanol, and the base is an inorganic base, such as $K_2CO_3$;

step c) is carried out by catalytic hydrogenation, i.e. by treatment with hydrogen in the presence of a palladium catalyst, preferably with Pd/C.

According to an even more preferred aspect, the present invention provides a process as described above, wherein in step a) the base is triethylamine, the solvent is N,N-dimethylformamide, the catalyst in combination with the ligand is selected from the group consisting of $PdCl_2(PPh_3)_2$, $PdCl_2(dppf)$ and $PdCl_2/XPhos$;

in step b) the base is $K_2CO_3$, the solvent is methanol, and the reduction of step c) is carried out by treatment with hydrogen in the presence of Pd/C, in tetrahydrofuran.

The above described process of the present invention is preferably carried out by isolating the intermediate compounds resulting from step a) and step b), namely compound of formula III and compound of formula II, respectively.

Also preferably, the process of the present invention is carried out without isolating intermediate compound of formula III.

Even more preferably, the process of the present invention is carried out as a one-pot reaction, without isolating neither the compound of formula III nor the compound of formula II. Therefore, the present invention also provides a process for preparing alectinib of formula I, or a pharmaceutically acceptable salt thereof, wherein the ethyl group present in formula I is introduced in a single step.

Typically, the compound of formula IV, as defined above, is reacted with trimethylsilylacetylene, a base, such as TEA, a palladium catalyst with a ligand, in a solvent, at a temperature in the range 50-100° C., preferably in the range 70-90° C., more preferably at about 80° C., and stirred until complete conversion of the reactant, typically for a time varying from 30 min to 24 hours. The reaction mixture is then typically cooled to room temperature and it is either submitted to work-up, to isolate intermediate of formula III, or to TMS cleavage conditions. In this second option, suitable base and solvent are added, for instance $K_2CO_3$ and methanol, and the reaction mixture is typically stirred for a time varying from 30 min to 6 hours until reaction completion. It is then typically either submitted to work-up, to isolate intermediate compound of formula II, or to reduction conditions to get the final product alectinib (I).

In the case the isolation of the intermediate compounds of formula III and/or of formula II is desired, the respective reaction mixture is worked-up. Such work-up involves standard methods, such as dilution, layers separation, precipitation, filtration, washing of solid residues, solvent concentrations, drying and all other methods well known to the person skilled in the art.

In the case the isolation of the compound of formula III is desired, the reaction mixture from step a) is worked-up. Such work-up typically involves precipitation of the reaction product by addition of an aqueous solution, filtration, washing of the solid with water, optionally washing with an organic solvent, for instance with cyclohexane or hexane or the like, or mixtures thereof, and drying under vacuum.

In the case the isolation of the compound of formula II is desired, the reaction mixture from step b) is worked-up. Such work-up typically involves precipitation of the reaction product by addition of an aqueous solution, filtration, washing of the solid with water, optionally washing with an organic solvent, or mixtures thereof, and drying under vacuum.

In the case the compound of formula II is not isolated, the reaction mixture from step b) is, for example, transferred in an autoclave, and a solvent and a catalyst are added, before filling with hydrogen, preferably at a pressure varying from 1 to 5 bars, more preferably at about 2-3 bar pressure. After stirring for a time typically varying from 1 to 24 hours, the reaction mixture is typically submitted to work-up, first by releasing hydrogen from the reactor, then filtering the catalyst. After evaporation of the solvents under vacuum, the final product is, for example, obtained by precipitation through addition of an aqueous solution, the solid product being then filtered and washed. Preferably, the product is washed with water and then with an organic solvent, or mixtures thereof, for instance with water and with cyclohexane, before drying under vacuum.

According to a preferred aspect, the present invention therefore provides a process for the preparation of alectinib, or a pharmaceutically acceptable salt thereof, as defined above, which comprises the steps of:

a) reacting a compound of formula IV as defined above with trimethylsilylacetylene in the presence of a base, a palladium catalyst and a ligand;
b) treating the crude from step a) with a base; and
c) treating the crude from step b) with hydrogen after addition of Pd/C.

Preferably, in step b) of the above process the base is $K_2CO_3$ and the reaction is carried out in the presence of an alcohol solvent. More preferably, the alcohol solvent is methanol.

Also preferably, in step a) of the above process the base is triethylamine, the palladium catalyst and ligand are selected from the group consisting of the combinations $PdCl_2(PPh_3)_2$, $PdCl_2(dppf)$ and $PdCl_2$/XPhos and the temperature is in the range 70-90° C. Even more preferably, in step a) the palladium catalyst and ligand combination is $PdCl_2(PPh_3)_2$ and the temperature is about 80° C. In addition, alectinib obtained by the process of the present invention may nonetheless be isolated by other methods, such as precipitation, cooling, filtration, centrifugation or combination thereof followed by optional washing with the water, solvent, a mixture of solvents or a mixture of solvent and water, or may be used directly for the preparation of pharmaceutically acceptable salts thereof.

Alectinib obtained by the process of present invention may optionally be purified by contacting alectinib with a solvent or a solvent mixture. Preferably, the solvent is selected from the group consisting of water; halogenated solvents such as dichloromethane, dichloroethane, chloroform; alcohols such as methanol, ethanol, propanol, isopropanol, isobutanol; or mixtures thereof. More preferably, alectinib is purified with alcoholic solvent or a mixture of halogenated and alcoholic solvents. Most preferably, alectinib is purified with methanol or a mixture of dichloromethane and methanol.

The alectinib obtained by the process of present invention, with or without purification, is optionally dried by the methods such as vacuum drying, heat drying, spray drying, freeze drying, supercritical drying or natural air drying. Any of the mentioned methods may also be used in combination to ensure removal of unbound solvent. Preferably the alectinib is dried by vacuum drying method. Preferably the drying is performed under vacuum and optionally under inert atmosphere, for example by passing a stream of warm inert gas such as nitrogen over or through the material.

The alectinib obtained by the process of present invention, with or without purification, is optionally converted into a pharmaceutically acceptable salt thereof, for instance the hydrochloride salt.

Alectinib hydrochloride is obtained for instance by contacting alectinib with a solvent, adding hydrochloric acid to the solution or suspension, and finally isolating alectinib hydrochloride. The solvent is preferably selected from the group consisting of alcohols, ketones, halogenated solvents, ethers, esters, nitriles or mixtures thereof; preferably the solvent is selected from the group consisting of methanol, ethanol, propanol, isopropanol, acetone, diisopropyl ketone, methylisobutyl ketone, methyl ethyl ketone, dichloromethane, dichloroethane, chloroform, tetrahydrofuran, 1,4-dioxane, ethylacetate, methylacetate, isopropyl acetate, acetonitrile or mixture thereof, more preferably solvent is selected from isopropanol, acetone, ethyl acetate, acetonitrile or a mixture of dichloromethane and methanol. Such contacting alectinib with a solvent may be carried out at 15 to 80° C.; preferably at room temperature for 30 minutes to 12 hours, preferably for 1-3 hours. The hydrochloric acid used may be added in form of concentrated solution, aqueous solution or in solution with a solvent, wherein solvent can be same or different as used in previous step. The alectinib hydrochloride thus obtained may be isolated by methods such as precipitation, cooling, filtration, centrifugation or combination thereof followed by optional washing it with the solvent or a mixture of solvents used during the process. The alectinib hydrochloride, thus obtained, is optionally dried by the methods such as vacuum drying, heat drying, spray drying, freeze drying, supercritical drying or natural air drying. Any of the mentioned methods may also be used in combination to ensure removal of unbound solvent. Preferably the alectinib hydrochloride is dried by vacuum drying method. As will be recognized, the drying time will be dependent upon, amongst other things, the amount of material to be dried, and the particular drying method used. Generally a drying time of 30 minutes to 20 hours, preferably 3 to 18 hours is sufficient. Preferably the drying is performed under vacuum and optionally under inert atmosphere, for example by passing a stream of warm inert gas such as nitrogen over or through the material.

According to the process of the present invention alectinib is provided in high overall yield as compared to processes known in the art.

The following examples describe specific embodiments of the present invention which will be clear and sufficient to the person skilled in the art. Optimum reaction conditions may vary with the particular reactants or solvent used, but such conditions can be determined by one skilled in the art by routine optimization procedures.

EXAMPLES

Detailed experimental parameters suitable for the preparation of alectinib or pharmaceutically acceptable salts thereof according to the present invention are provided by the following examples, which are intended to be illustrative and not limiting.

Preparations of alectinib are herein described starting from compound of formula IV (compound IV). For the preparation of 9-bromo-6,6-dimethyl-8-(4-morpholinopiperidin-1-yl)-11-oxo-6,11-dihydro-5H-benzo-[b]carbazole-3-carbonitrile (compound of formula IV) is made reference to WO2010/143664 and to Bioorg. Med. Chem., 2012, 20, 1271-1280.

Unless otherwise noted, all materials, solvents and reagents, including anhydrous solvents such as DMF and THF, were obtained from commercial suppliers, of the best grade, and used without further purification. All reactions involving air- or moisture-sensitive compounds were performed under nitrogen or argon atmosphere, unless otherwise noted.

NMR Spectra were recorded with Varian Mercury Plus 400 or Unity Inova 600 MHz spectrometers. Chemical shifts were reported as δ values (ppm) relative to the solvent peak of DMSO-$D_6$ set at δ=2.50 ppm ($^1$H-NMR) or δ=39.5 ppm ($^{13}$C-NMR). Coupling constants are given in Hertz.

LC-MS analyses were performed on an HP1100 liquid chromatograph coupled with an electrospray ionization-mass spectrometer (Agilent Technologies MSD1100 single-quadrupole mass spectrometer) using a Phenomenex Gemini C18—3μ-110 Å column, $H_2O/CH_3CN$ as eluent at 25° C. (positive scan 100-500 m/z, fragmentor 70 eV).

Analytical data for compounds IV and I are in agreement with the data reported in the prior art (Kinoshita, K. et al. Bioorganic and *Medicinal Chemistry,* 2012, 20, 1271-1280).

Example 1

Preparation in Three Steps, with Isolation of Compound of Formula III

Step a and b

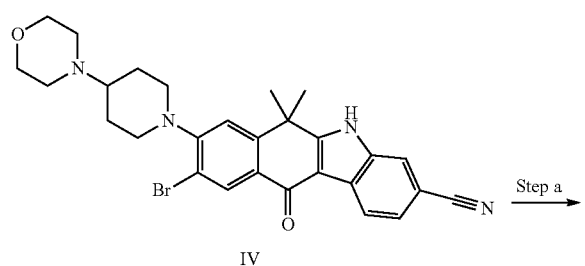

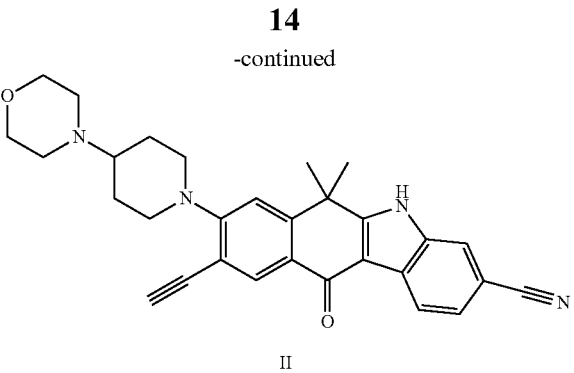

Step c

Step a—Alkynylation: Preparation of Compound of Formula III 9-(trimethylsilyl)ethynyl-6,6-dimethyl-8-(4-morpholin-4-yl-piperidin-1-yl)-11-oxo-6,11-dihydro-5H-benzo[b]carbazole-3-carbonitrile (III)

In a dry Schlenk tube, the reactants were added, under nitrogen, in the following order: compound IV (1.07 g, 2 mmol), $PdCl_2(PPh_3)$ (2 mol %), trimethylsilylacetylene (2.5 eq, 712 μL), TEA (2 eq, 558 μL), and DMF (13 mL). The Schlenk tube was closed and transferred in an oil bath at 80° C. The reaction was stirred until complete conversion of compound IV (8-12 h). The reaction mixture was cooled at room temperature, filtered on charcoal and washed with DMF (2×5 mL). Water (60 mL) was added to the reaction crude to obtain a yellow precipitate, which was filtered, washed with water (3×10 mL) and then dried under vacuum (yield 74%, 816 mg).

$^1$H NMR (400 MHz, $CDCl_3$, 25° C.): δ=0.26; (s, 9H, $Me_3Si$), 1.64; (m, 2H, $H_{10}$), 1.76; (s, 6H, $H_5$+$H_6$), 1.80; (m, 2H, $H_{10}$), 2.42; (m, 1H, $H_{13}$), 2.87; (m, 2H, $H_9$), 3.31; (m, 4H, $H_{11}$), 3.63; (m, 4H, $H_{12}$), 3.95; (m, 2H, $H_9$), 7.23; (s, 1H, $H_7$), 7.59; (d, 1H, J=8.0 Hz, $H_2$), 8.00; (s, 1H, $H_3$), 8.11; (s, 1H, $H_8$), 8.30; (d, 1H, J=8.0 Hz, $H_1$), 12.75; (s, 1H, NH).

LC-MS (ESI): r.t. 6.4 min, m/z=551 [M+1], 1101 [2M+1].

Step b—Cleavage: Preparation of Compound of Formula II 9-ethynyl-6,6-dimethyl-8-(4-morpholin-4-yl-piperidin-1-yl)-11-oxo-6,11-dihydro-5H-benzo[b]carbazole-3-carbonitrile (II)

In a one-neck vessel, the white solid obtained from step a (816 mg, 1.48 mmol) was added to MeOH (15 mL) and $K_2CO_3$ (3 eq., 614 mg). The cloudy solution was stirred at room temperature for 1-2 hours until reaction completion, and then water (60 mL) was added. The stirring was continued for further about 30 minutes to obtain a pale yellow solid, which was filtered, washed with water (2×30 mL), and with MeOH (15 mL). After drying under vacuum the white solid was isolated in 90% yield (637 mg).

$^1$H NMR (400 MHz, $CDCl_3$, 25° C.): δ=1.56; (m, 2H, $H_{10}$), 1.76; (s, 6H, $H_5+H_6$), 1.90; (bd, J=9.2 Hz, 2H, $H_{10}$), 2.34; (m, 1H, $H_{13}$), 2.84; (m, 2H, $H_9$), 3.32; (m, 4H, $H_{11}$), 3.59; (m, 4H, $H_{12}$), 3.86; (m, 2H, $H_9$), 4.50; (s, 1H, HC≡C—), 7.24; (s, 1H, $H_7$), 7.60; (d, 1H, J=8.0 Hz, $H_2$), 8.00; (s, 1H, $H_3$), 8.14; (s, 1H, $H_8$), 8.30; (d, 1H, J=8.0 Hz, $H_1$), 12.72; (s, 1H, NH).

LC-MS (ESI): r.t. 1.94 min, m/z=479 [M+1].

Step c—Catalytic Hydrogenation: Preparation of Alectinib (I)

The white solid obtained from step b (1.33 mmol, 637 mg) was diluted under nitrogen with dry THF (18 mL). The solution was transferred in an autoclave, and Pd/C 10% (10 mol %, 13 mg) was added to the reaction mixture. The autoclave was filled with $H_2$ at 2.5 bar pressure and the reaction was stirred for 8 hours at room temperature. Hydrogen was then released from the reactor and the reaction mixture was filtered onto a celite pad, which was then washed with MeOH (15 mL). The organic layer was evaporated under vacuum. Water (80 mL) was added to the reaction crude to obtain an-off white precipitate, that was filtered and washed with water (2×30 mL). After drying under vacuum the solid was recrystallized from hot MeOH (8 mL). The pure product was obtained as an off-white solid in 89% yield (1.18 mmol, 570 mg).

$^1$H NMR (400 MHz, $CDCl_3$, 25° C.): δ=1.26; (t, 3H, J=7.6 Hz, $CH_3CH_2$), 1.60; (m, 2H, $H_{10}$), 1.73; (s, 6H, $H_5+H_6$), 1.90; (bd, J=10.8 Hz, 2H, $H_{10}$), 2.28; (m, 1H, $H_{13}$), 2.69; (q, 2H, J=7.6 Hz, $CH_3CH_2$), 2.74; (m, 2H, $H_9$), 2.89 (m, 2H, $H_{11}$), 3.20; (m, 2H, $H_9$), 3.38; (m, 2H, $H_{11}$), 3.60; (m, 4H, $H_{12}$), 7.22 (s, 1H, $H_7$), 7.47; (d, 1H, J=8.0 Hz, $H_2$), 7.87; (s, 1H, NH), 7.92; (s, 1H, $H_3$), 8.04; (s, 1H, $H_8$), 8.31; (d, 1H, J=8.0 Hz, $H_1$).

LC-MS (ESI): r.t. 1.48 min, m/z=483 [M+1].

Example 2

Preparation in Two Steps, without Isolation of Compound of Formula III

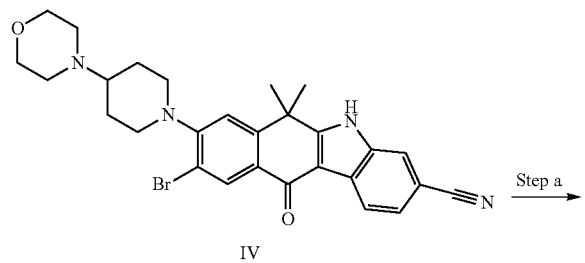

IV

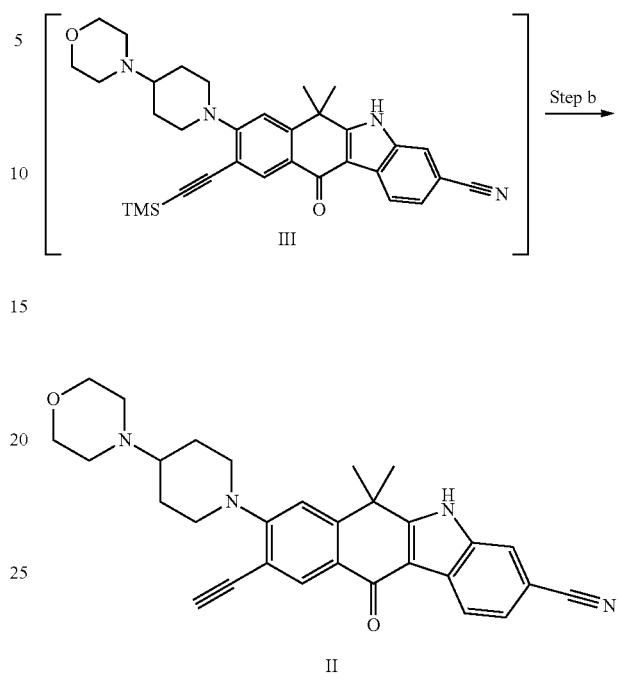

Step a-b—Alkynylation and Cleavage: Preparation of Compound of Formula II

In a dry Schlenk tube, the reactants were added, under nitrogen, in the following order: compound IV (1.07 g, 2 mmol), $PdCl_2(PPh_3)$ (2 mol %), trimethylsilylacetylene (2.5 eq, 712 µL), TEA (2 eq, 558 µL), and DMF (13 mL). The Schlenk tube was closed and transferred in an oil bath at 80° C. The reaction was stirred until complete conversion of compound IV. The tube was removed from the oil bath, the reaction mixture was filtered on charcoal and washed with DMF (2×5 mL). Then MeOH (15 mL) and $K_2CO_3$ (3 eq., 614 mg) were added to the DMF solution and stirring was continued at room temperature until reaction completion. Water (60 mL) was slowly added to the reaction crude to obtain a yellow precipitate, which was filtered, washed with methanol (3×10 mL) and then dried under vacuum (717 mg, 1.50 mmol, 75%).

Step c—Catalytic Hydrogenation: Preparation of Alectinib

The white solid obtained from step 1 (1.5 mmol, 717 mg) was diluted under nitrogen with dry THF (20 mL). The solution was transferred in an autoclave, and Pd/C 10% (10 mol %, 15 mg) was added to the reaction mixture. The autoclave was filled with $H_2$ at 2.5 bar pressure and the reaction was stirred for 8 hours. Hydrogen was then released from the reactor and the reaction mixture was filtered onto a celite pad, which was washed with MeOH (15 mL). The organic layer was evaporated under vacuum. Water (80 mL) was added to the reaction crude to obtain an off-white precipitate, that was filtered and washed with water (2×30 mL). After drying under vacuum the solid was recrystallized from hot MeOH (9 mL). The pure product was obtained as an off-white solid in 89% yield (1.33 mmol, 644 mg).

Example 3

Preparation of Alectinib in One-Pot Procedure

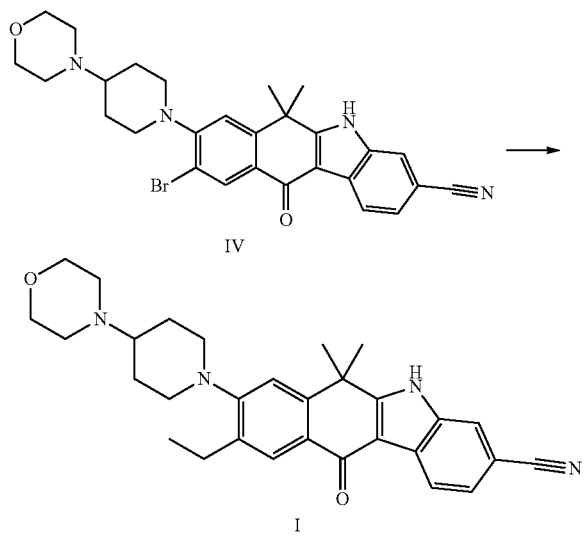

In a dry Schlenk tube, the reactants were added, under nitrogen, in the following order: compound IV (160 mg, 0.3 mmol), PdCl$_2$(PPh$_3$) (4.3 mg, 2 mol %), trimethylsilylacetylene (106 µl, 2.5 eq), TEA (85 µl, 2 eq.), and DMF (2 mL). The Schlenk tube was closed and transferred in an oil bath at 80° C. The reaction was stirred until complete conversion of reactant. The tube was removed from the oil bath and cooled at room temperature. Under nitrogen, MeOH (1 mL) and K$_2$CO$_3$ (125 mg, 3 eq.) were added and the reaction was stirred for 2 hours. The solution was transferred in an autoclave, and THF (4 mL) and Pd/C 10% (10 mol %, 31 mg) were added to the reaction mixture. The autoclave was filled with H$_2$ at 2.5 bar pressure and the reaction was stirred for 8 hours.

Hydrogen was released from the reactor and the reaction mixture was filtered onto a celite pad and transferred in a flask. The solvents were evaporated under vacuum. Water (20 mL) was added to the reaction crude to obtain an off-white precipitate, which was filtered, washed with water (2×10 mL), and then dried under vacuum. The solid was recrystallized from hot MeOH (2 mL). The pure product was obtained as an off-white solid (100 mg, 69% yield).

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A process for preparing alectinib of formula I,

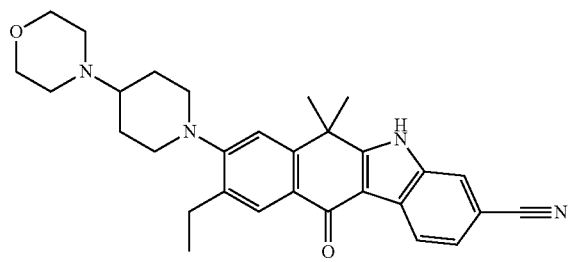

or a pharmaceutically acceptable salt thereof, the process comprising:

a) reacting a compound of formula IV

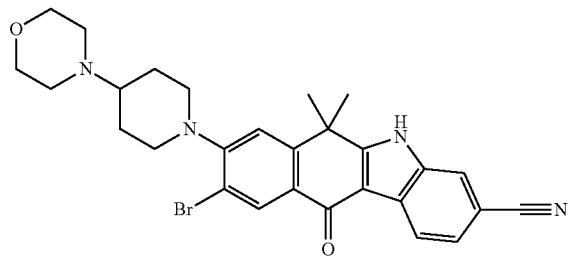

with trimethylsilylacetylene in the presence of a base, and a palladium catalyst optionally comprising a ligand;

b) treating the resulting intermediate compound of formula III

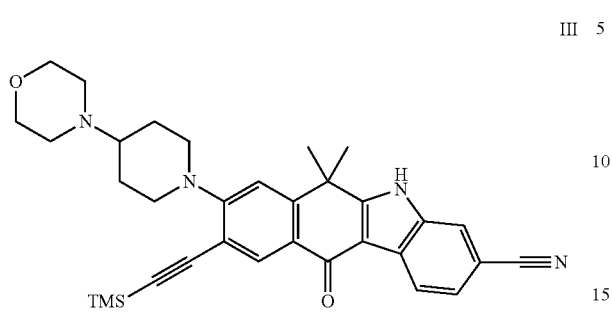

with a base; and c) converting the resulting intermediate compound of formula II:

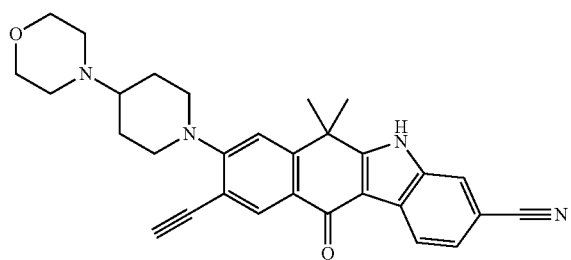

into alectinib, or a pharmaceutically acceptable salt thereof, by reduction of the ethynyl group.

2. The process according to claim 1, wherein
step a) is carried performed a temperature of 70-90° C. and the base is an organic base;
step b) is performed in an alcohol solvent and the base is an inorganic base.

3. The process according to claim 1, wherein the reduction is performed by treatment with hydrogen in the presence of Pd/C.

4. The process according to claim 2, wherein the inorganic base comprises $K_2CO_3$ and the alcohol solvent comprises methanol.

5. The process according to claim 2, wherein the organic base comprises triethylamine.

6. The process according to claim 2, wherein step a) is performed in a solvent comprising N,N-dimethylformamide.

7. The process according to claim 1, wherein the palladium catalyst comprises $PdCl_2(PPh_3)_2$, $PdCl_2(dppf)$, $PdCl_2$/XPhos, or a combination thereof.

8. The process according to claim 2, wherein step a) is performed at a temperature of 75-85° C.

9. The process according to claim 1, wherein the reduction is performed in a solvent comprising tetrahydrofuran.

10. The process according to claim 1, wherein the steps a), b) and c) are performed as a one-pot process.

11. The process according to claim 2, wherein the organic base comprises triethylamine, the palladium catalyst comprises $PdCl_2(PPh_3)_2$, the inorganic base comprises $K_2CO_3$, the alcohol solvent comprises methanol, and the reduction is performed by treatment with hydrogen in the presence of Pd/C in a solvent comprising tetrahydrofuran.

12. A process for preparing alectinib of formula I,

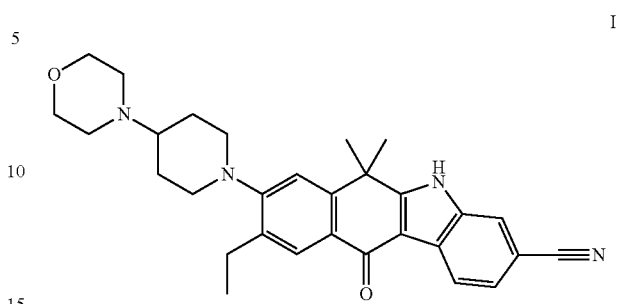

or a pharmaceutically acceptable salt thereof, the process comprising:

a) reacting a compound of formula IV

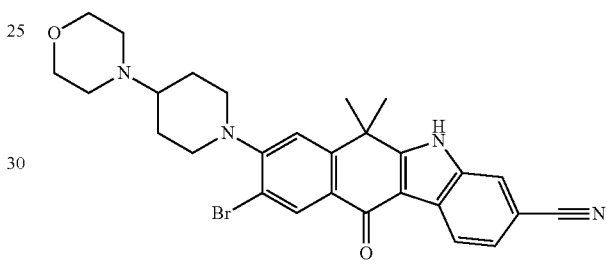

with trimethylsilylacetylene in the presence of a base, and a palladium catalyst optionally comprising a ligand;

b) treating the crude product from step a) with a base; and c) treating the crude product from step b) with hydrogen after addition of Pd/C.

13. The process according to claim 12, wherein, in step a), the base comprises triethylamine, the palladium catalyst comprises $PdCl_2(PPh_3)_2$, $PdCl_2(dppf)$, $PdCl_2/XPhos$, or a combination thereof, and the temperature is 70-90° C., and in step b), the base comprises $K_2CO_3$ and the reaction is performed in the presence of an alcohol solvent.

14. A compound of formula III

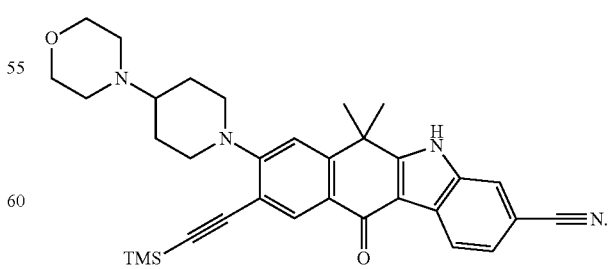

15. A method for preparing alectinib, comprising converting the compound of formula III as defined in claim 14 into alectinib.

16. The method of claim 15, comprising converting the compound of formula III into a compound of formula II:
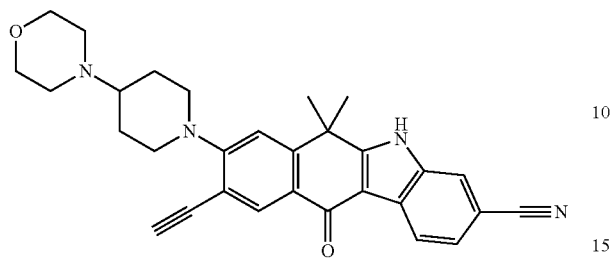
and converting the compound of formula II into alectinib.
* * * * *